(12) United States Patent
Zhong et al.

(10) Patent No.: US 9,456,835 B2
(45) Date of Patent: Oct. 4, 2016

(54) METHODS AND APPARATUSES FOR GENERATING A STEERABLE PRESSURE FIELD IN A SHOCK WAVE LITHOTRIPTER

(75) Inventors: Pei Zhong, Chapel Hill, NC (US); Walter Neal Simmons, Durham, NC (US); Georgy N. Sankin, Durham, NC (US); Nathan Smith, Durham, NC (US); Franklin Hadley Cocks, Durham, NC (US); Glenn M. Preminger, Chapel Hill, NC (US)

(73) Assignee: DUKE UNIVERSITY, Durham, NC (US)

( * ) Notice: Subject to any disclaimer, the term of this patent is extended or adjusted under 35 U.S.C. 154(b) by 854 days.

(21) Appl. No.: 13/428,937

(22) Filed: Mar. 23, 2012

(65) Prior Publication Data
US 2013/0046210 A1   Feb. 21, 2013

Related U.S. Application Data

(63) Continuation of application No. PCT/US2010/050209, filed on Sep. 24, 2010.

(60) Provisional application No. 61/245,448, filed on Sep. 24, 2009.

(51) Int. Cl.
*A61H 1/00* (2006.01)
*A61B 17/225* (2006.01)

(52) U.S. Cl.
CPC .................... *A61B 17/225* (2013.01)

(58) Field of Classification Search
CPC ............... A61B 17/2251; G10K 15/06
See application file for complete search history.

(56) References Cited

U.S. PATENT DOCUMENTS

| | | | |
|---|---|---|---|
| 4,622,969 A | 11/1986 | Forssmann et al. | |
| 4,655,205 A | 4/1987 | Hepp et al. | |
| 4,807,627 A | 2/1989 | Eisenmenger | |
| 2004/0068209 A1 | 4/2004 | Matula et al. | |
| 2005/0234388 A1* | 10/2005 | Amos et al. | 604/8 |
| 2009/0088670 A1 | 4/2009 | Warlick et al. | |

FOREIGN PATENT DOCUMENTS

DE   37 03 337 C2   4/1996

OTHER PUBLICATIONS

International Search Report and Written Opinion for PCT/US2010/050209 dated Nov. 30, 2010.

* cited by examiner

*Primary Examiner* — Tse Chen
*Assistant Examiner* — Hien Nguyen
(74) *Attorney, Agent, or Firm* — Jenkins, Wilson, Taylor & Hunt, P.A.

(57) ABSTRACT

Lithotripter apparatuses and methods are provided for selectively modifying an acoustic pressure field and can include a shock wave source operable to generate a shock wave having a substantially axisymmetric acoustic pressure field, an acoustic focusing member positioned between the shock wave source and a target, and an acoustic barrier positioned between the shock wave source and the acoustic focusing member. The acoustic barrier can be operable to selectively block a portion of the shock wave generated by the shock wave source such that the substantially axisymmetric pressure field is transformed into a modified acoustic pressure field.

6 Claims, 8 Drawing Sheets

METHODS AND APPARATUSES FOR GENERATING A STEERABLE PRESSURE FIELD IN A SHOCK WAVE LITHOTRIPTER

CROSS-REFERENCE TO RELATED APPLICATIONS

This application is a continuation of and claims priority to PCT/US2010/050209 filed Sep. 24, 2010, which claims the benefit of and priority to U.S. Provisional Application No. 61/245,448, filed Sep. 24, 2009, the entire disclosure of which is herein incorporated by reference.

GOVERNMENT INTEREST

This invention was made with U.S. Government support under Grant No. 5RO1-DK052985 awarded by the National Institutes of Health/National Institute of Diabetes and Digestive and Kidney Diseases. The U.S. Government has certain rights in the invention.

TECHNICAL FIELD

The subject matter disclosed herein relates generally to shock wave lithotripters and methods of using shock wave lithotripters. More particularly, the subject matter disclosed herein relates to apparatuses and methods for selectively blocking shock waves generated from a shock wave source to generate a modified acoustic pressure field.

BACKGROUND

Shock wave lithotripters utilize high-energy focused shock waves to disintegrate concretions located in the upper urinary track and kidney of a patient. Recent studies have demonstrated that a lithotripter with a broad beam size (defined by the −6 dB of the peak pressure distribution in the focal plane of the lithotripter) can generate better stone comminution than its counterpart with a narrow beam size under the same effective acoustic pulse energy. This observation can be attributed to several factors, including lateral spreading of residual stone fragments, stone movement due to respiratory motion, and practical difficulties in accurate alignment of the stone to lithotripter focus during clinical treatment. Hence, broadening the traverse beam size of the lithotripter in its focal plane can benefit stone comminution.

However, enlargement of the traverse beam size in the focal plane is generally limited by the simultaneous increase in the longitudinal beam size of the lithotripter along the axis of the incident shock wave. This later parameter determines the pressure amplitude at the patient's flank, and therefore correlates with discomfort and skin lesion produced at the shock wave entrance/exit sites during clinical shock wave lithotripsy (SWL). Independent of the design, all modern clinical shock wave lithotripters produce an axisymmetric acoustic field around the central axis of the shock source. As a result, enlargement of the transverse beam size is severely limited in current clinical shock wave lithotripters.

To date, no practical methods have been developed to solve this problem. Interestingly, the pressure distribution in the focal plane of the original Dornier HM-3TM lithotripter (Friedrichshafen; W. Germany) is also non-axisymmetric with a broader beam size in the head-foot direction (~12 mm) and a narrower one in the transverse direction (~9 mm). This non-axisymmetric pressure distribution is presumably caused by the truncation of the ellipsoidal reflector at the lateral sides to accommodate the bi-planar fluoroscopy for stone localization, which may contribute to the effectiveness of the HM-3. However, the acoustic field in an HM-3 lithotripter cannot be controlled to steer in a designated orientation. Moreover, the eccentricity of the pressure field in an HM-3 lithotripter cannot be adjusted except for some random variations caused by the non-repeatable spark discharge at the tip of the HM-3 electrode.

Therefore, it would be beneficial to provide a lithotripter that is able to enlarge the effective transverse beam size without increasing the longitudinal beam size of the shock wave lithotripter. It would also be beneficial to provide a lithotripter that is steerable.

SUMMARY

In accordance with this disclosure, apparatuses and methods for selectively blocking shock waves generated from a shock wave source to generate a modified acoustic pressure field are provided. In one aspect, a lithotripter for producing a steerable acoustic pressure field is provided. The lithotripter can comprise a shock wave source operable to generate a shock wave having a substantially axisymmetric acoustic pressure field, an acoustic focusing member positioned between the shock wave source and a target, and an acoustic barrier positioned between the shock wave source and the acoustic focusing member. The acoustic barrier can be operable to selectively block a portion of the shock wave generated by the shock wave source such that the substantially axisymmetric pressure field is transformed into a modified (e.g., non-axisymmetric) acoustic pressure field.

In another aspect, a method for selectively modifying an acoustic pressure field is provided. The method can comprise generating a shock wave having a substantially axisymmetric acoustic pressure field from a shock wave source, positioning one or more acoustic barriers in a path of the shock wave, and selectively blocking a portion of the shock wave to transform the substantially axisymmetric acoustic pressure field into a modified acoustic pressure field.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the subject matter disclosed herein will be more readily understood from the following detailed description which should be read in conjunction with the accompanying drawings that are given merely by way of explanatory and non-limiting example, and in which.

DETAILED DESCRIPTION

The subject matter disclosed herein provides shock wave lithotripters and methods of using shock wave lithotripters. For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

Figure 1:
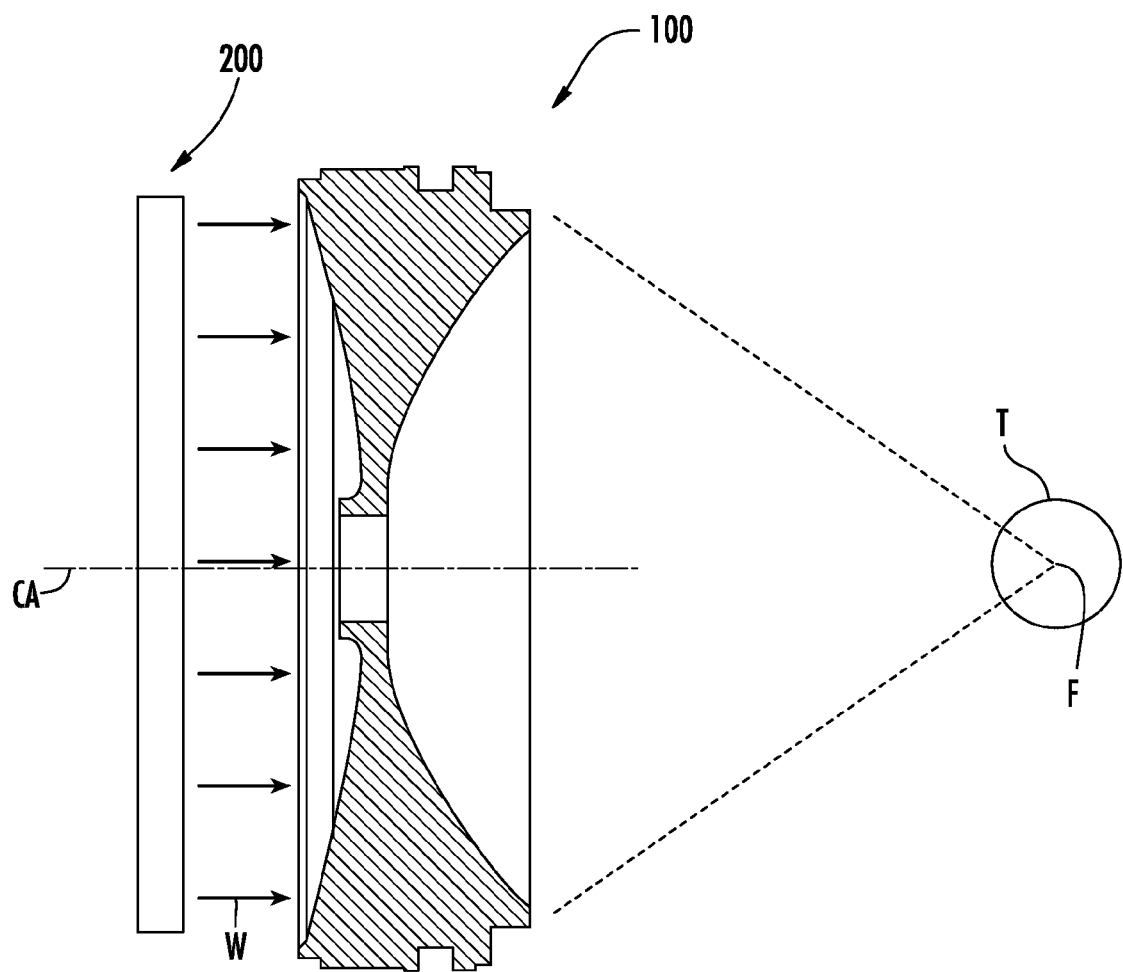
FIG. 1 is a side view of a prior art lithotripter for use in shock wave lithotripsy.

FIG. 1 shows a design for a typical lithotripter in which an acoustic focusing member, generally designated 100, is positioned between a shock wave source, generally designated 200 (e.g., an electromagnetic coil), and a target T (e.g., a patient's body). In this arrangement, acoustic shock waves W generated by shock wave source 200 can be directed towards target T positioned at a beam focus F. Specifically, for example, acoustic focusing member 100 can be an acoustic lens positioned directly between shock wave source 200 and target T for focusing shock waves W toward beam focus F, or it can be an acoustic reflector positioned around shock wave source 200 for redirecting shock waves W toward beam focus F. In either configuration, the resulting shock wave W is supplied to its intended destination (e.g., target T) via a corresponding acoustic propagation medium, such as degassed water. As discussed above, this arrangement is limited in the sense that it produces a substantially axisymmetric (i.e., circular) acoustic field centered at a central axis CA of shock wave source 200. In contrast, the present subject matter provides a lithotripter apparatus that is steerable such that it can be selectively operable to produce a pressure field that is shaped differently than the centered, substantially circular field produced by conventional lithotripters. Such an apparatus can be used to improve stone comminution while concomitantly reducing collateral tissue injury during non-invasive treatment of kidney stones in a patient. Further, the features described herein can be adapted to fit currently used clinical shock wave lithotripters with minimal increase in manufacturing costs and component susceptibility to damage during the routine operation of the shock wave lithotripter.

As used herein, the term "shock wave source" refers to that portion of a lithotripter machine that generates shock waves. It is to be understood that the concepts provided herein can be applied to any of a variety of different types of lithotripters, such as electromagnetic (EM) shock wave lithotripters, electrohydraulic shock wave lithotripters, piezoelectric shock wave lithotripters, and the like. In electromagnetic lithotripsy, the shock wave source normally consists of an electrically conductive membrane and a flat coil situated opposite it. The shock waves are generated by connecting the flat coil to a high-voltage supply (e.g., a capacitor which is charged to several kV). The discharge current flows through the flat coil, rapidly building up a magnetic field to that generates a current in the membrane that is opposite to that of the flat coil. In this way, an opposing magnetic field is built up and moves the membrane abruptly away from the flat coil. Electrohydraulic lithotripsy utilizes a probe containing two electrodes separated by an area of insulation. While electric current is passed between the two electrodes, a spark is created which vaporizes the water or other surrounding fluids at the end of the probe. This spark gap creates a cavitation bubble, which rapidly expands, creating a shock wave. In piezoelectric lithotripsy, the shock wave source comprises transducers consisting of piezoelectric elements (e.g., crystals, ceramics, etc.) that are arranged on the inner surface of a hemispheric dish with each element aligned towards the center of the curvature of a sphere to produce acoustic waves that aimed at the focal point. Oscillation of the piezoelectric elements are induced by electric stimulation, and the shock wave energy is conducted along a water path.

Figure 2:
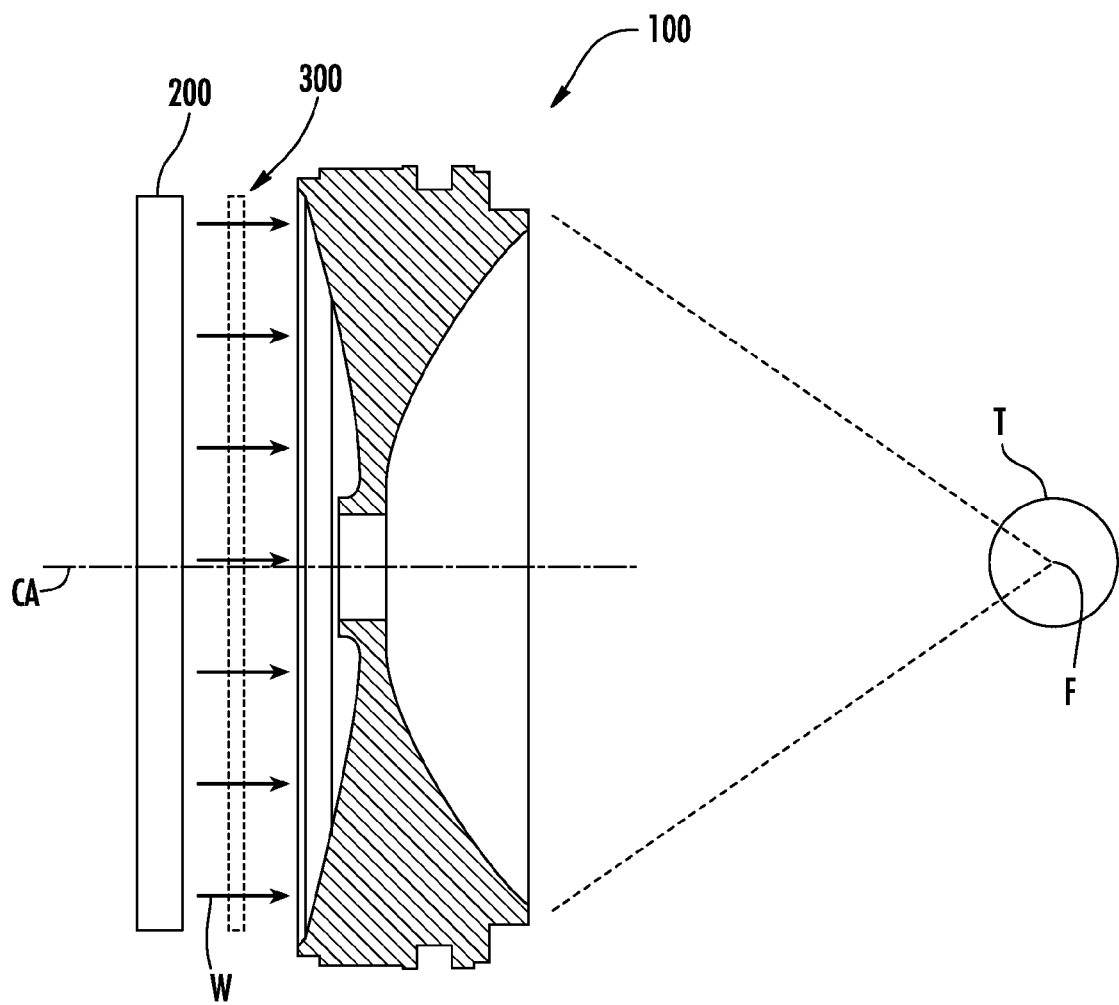
FIG. 2 is a side view of a lithotripter according to an embodiment of the subject matter disclosed herein.

Regardless of the specific lithotripsy method employed, a lithotripter according to the subject matter disclosed herein can have the general arrangement shown in FIG. 2. An acoustic focusing member 100 can be positioned between a shock wave source 200 and a target T. Contrary to conventional arrangements, however, a lithotripter according to the present subject matter can further comprise an acoustic barrier, generally designated 300, positioned between shock wave source 200 and acoustic focusing member 100.

As used herein, the term "acoustic barrier" refers to any structure or material layer capable of absorbing, reflecting, or otherwise diverting shock waves. Such a barrier may be able to absorb shock wave energy in numerous ways, including (1) friction between fibers of a porous material or in the voids of a non-fibrous material (e.g., a dissipative absorber); (2) a membrane absorber which works by vibration of a highly damped panel; and/or (3) a tuned cavity absorber, working on the principle of Helmholz resonance. Suitable materials for use include, but are not limited to, cork, elastomer or other polymer membranes, foam insulation, thin metallic membranes with a thin air gap in between, and the like. In some aspects, the acoustic barrier material can have a high acoustic attenuation coefficient. In other aspects, the acoustic barrier material can have a large acoustic impedance mismatch with water (i.e., acoustic mask) such that it can impede the transmission of the shock wave coming out from the portion of the shock wave source.

By selectively absorbing, deflecting, or otherwise distorting the shock waves W generated by shock wave source 200, a lithotripter according to the subject matter disclosed herein can transform the resulting pressure field to have a shape that is different than the centered, substantially circular field produced by conventional lithotripters. For example, the acoustic pressure field can be modified to have a substantially elliptical or otherwise oblong shape, a substantially circular (i.e., axisymmetric) shape that is offset from central axis CA of shock wave source 200, or any other shape that has a relatively broader beam size in at least one region of the acoustic pressure field. In this way, a lithotripter according to the subject matter disclosed herein can be used to specifically target concretions having a particular shape or being located in a particular region of the upper urinary track or kidney of a patient.

Figure 3B:
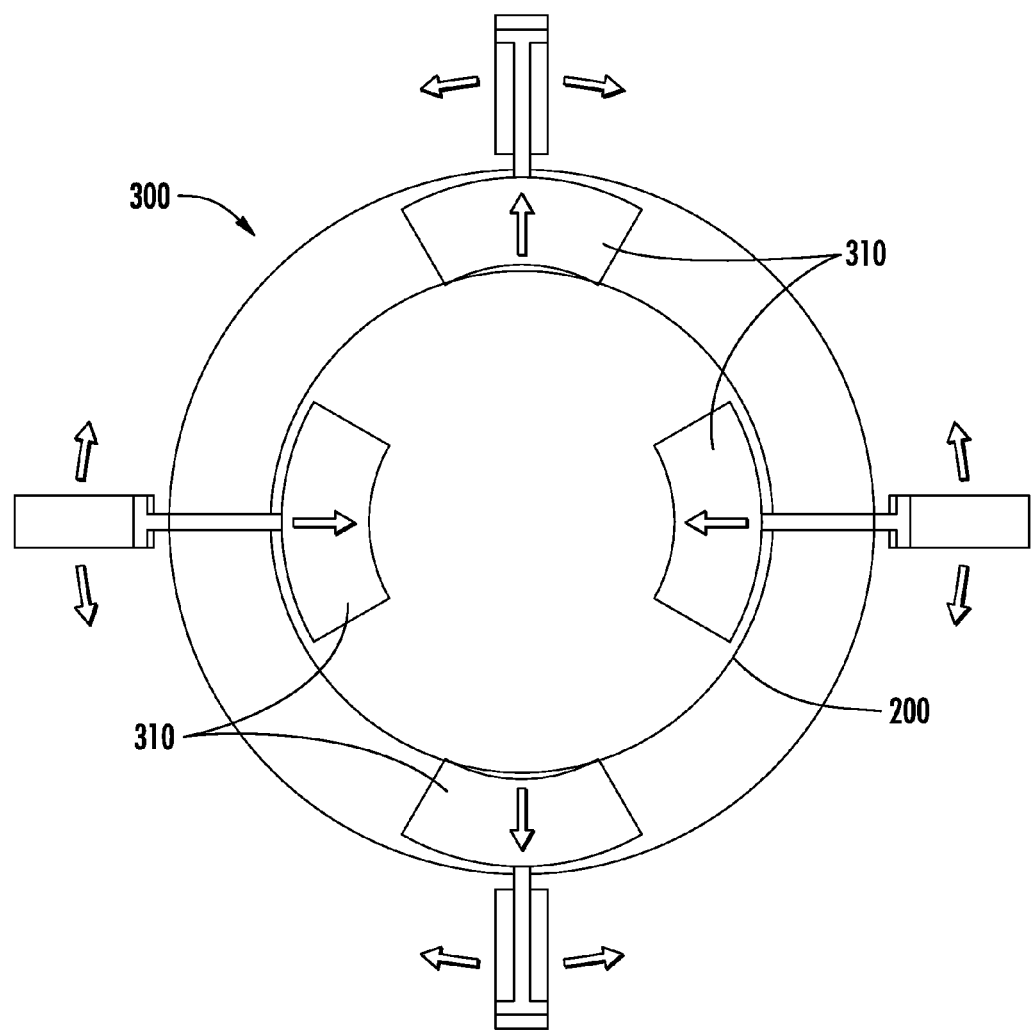
FIGS. 3B and 3C are top views of the lithotripter of FIG. 3A in two different operating configurations.
Figure 3A:
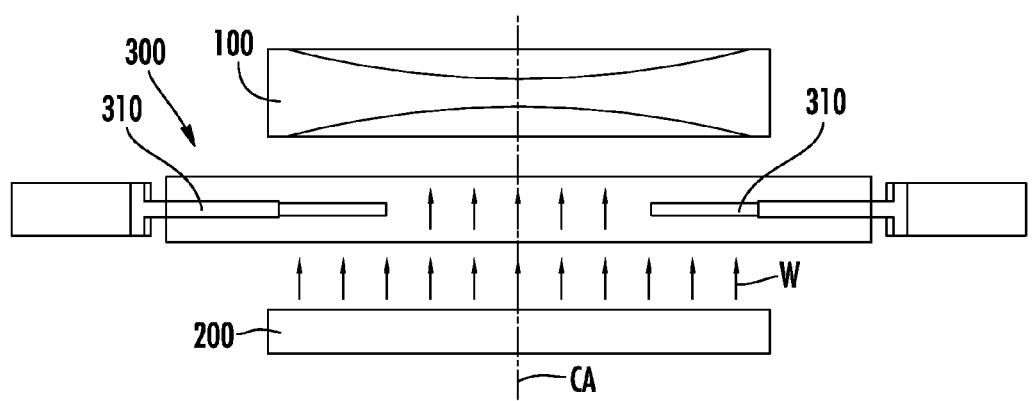
FIG. 3A is a cutaway side view of a lithotripter having an acoustic barrier comprising a plurality of non-deformable elements according to an embodiment of the subject matter disclosed herein.
Figure 3C:
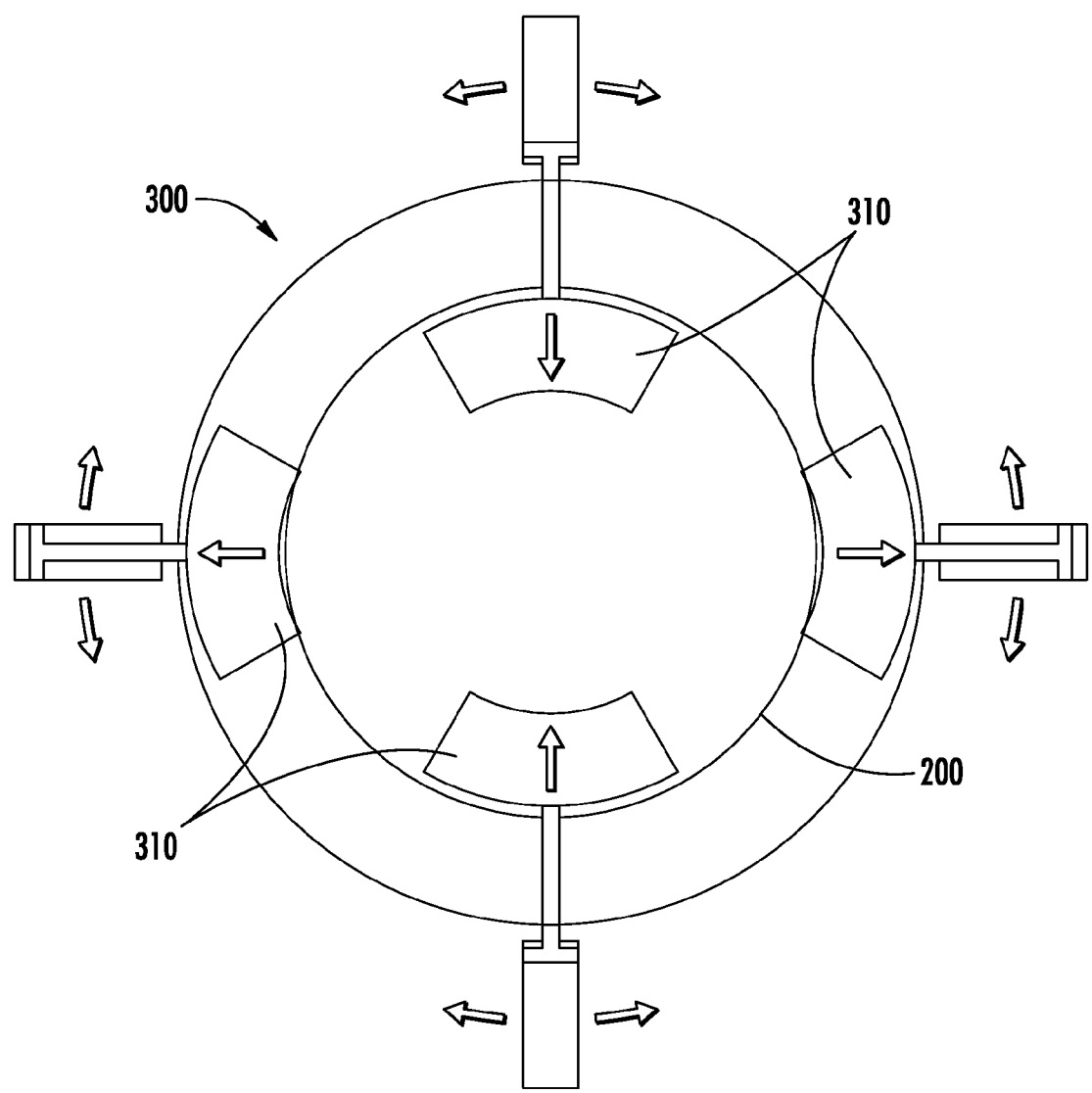

For instance, in one particular configuration shown in FIGS. 3A through 3C, acoustic barrier 300 can comprise one or more non-deformable elements 310 positioned between acoustic focusing member 100 and shock wave source 200. As used herein, the term "non-deformable" is not intended to connote an absolute resistance to strain under application of a stress. Rather, "non-deformable" refers to a substantially solid element having a defined geometry. Non-deformable elements 310 can be composed of a material that has an acoustic impedance mismatch with the acoustic propagation medium in which the lithotripter is located. For example, non-deformable elements 310 can comprise cork, foam insulation, or a similar material. In addition, non-deformable elements 310 can be provided in any shape or size that produces a desirable modified acoustic pressure field. For instance, the shape and size of non-deformable elements 310 can be also be chosen based on the type of lithotripter used and can be readily determined by those skilled in the art.

Further, in some configurations, non-deformable elements 310 can be rotated by a flow driven or magnetically activated motion during shock wave lithotripsy to thereby rotate the modified acoustic pressure field. Specifically, non-deformable elements 310 can be moved in a circular or wobbling pattern to create a large "effective" beam size and fragmentation area over a typical treatment duration of, for example, 2,000 to 3,000 shocks. Such a non-uniform and rotating pressure field can also increase the effectiveness of individual pulses on stone comminution. Based on the principle of fracture mechanics, there is an optimal orientation between the applied stress and the axis of a pre-existing flaw in the material to produce failure under minimally applied stress. Considering that numerous flaws having different orientations may exist in kidney stones, it can be beneficial to apply the maximum pressure from different orientations rather than only from a single direction.

Alternatively, non-deformable elements 310 can be positioned in fixed locations between acoustic focusing member 100 and shock wave source 200 to achieve a constant beam having a desired modified acoustic pressure field, for example and without limitation, a non-axisymmetric pressure field. Such configurations may be useful in the treatment of renal and ureteral calculi when the beam size needs to be aligned to match closely with the internal structure of the kidney and urinary track or with the direction of the respiratory motion of the kidney.

In yet a further alternative configuration, as shown in FIGS. 3A through 3C, non-deformable elements 310 can be rotationally fixed relative to central axis CA of shock wave source 200 but can be movable in a radial direction to extend into or out of the path of shock waves W generated from shock wave source 200. For instance, acoustic barrier 300 can comprise a plurality of non-deformable elements 310 spaced at regular intervals about central axis CA of shock wave source 200 and independently movable toward or away from central axis CA. As shown in FIGS. 3B and 3C, for example, acoustic barrier 300 can comprise four non-deformable elements 310 spaced apart by 90°.

Where there are even numbers of non-deformable elements 310 as in this configuration, opposing pairs of non-deformable elements 310 can be alternately extended and retracted to generate a substantially elliptical acoustic pressure field that is aligned with the respective pair of non-deformable elements 310 that is extended at that time. The selection of which of the opposing pairs of non-deformable elements 310 that is extended can be alternated to effectively "rotate" the substantially elliptical acoustic pressure field by 90° increments. Alternatively, any number of non-deformable elements 310 can be provided, and they can be actuated in any sequence to achieve a desirable modified acoustic pressure field, for example and without limitation, a non-axisymmetric pressure field. Specifically, for example, an elliptical pressure contour created by the extension of selected non-deformable elements 310 into the path of shock waves W can be rotated around the lithotripter axis at a constant rate. For instance, six pairs of opposing non-deformable elements 310 activated in sequence can result in the modified acoustic pressure field being rotated 30° at a time at predefined intervals (e.g., about every 50 shocks).

Figure 4:
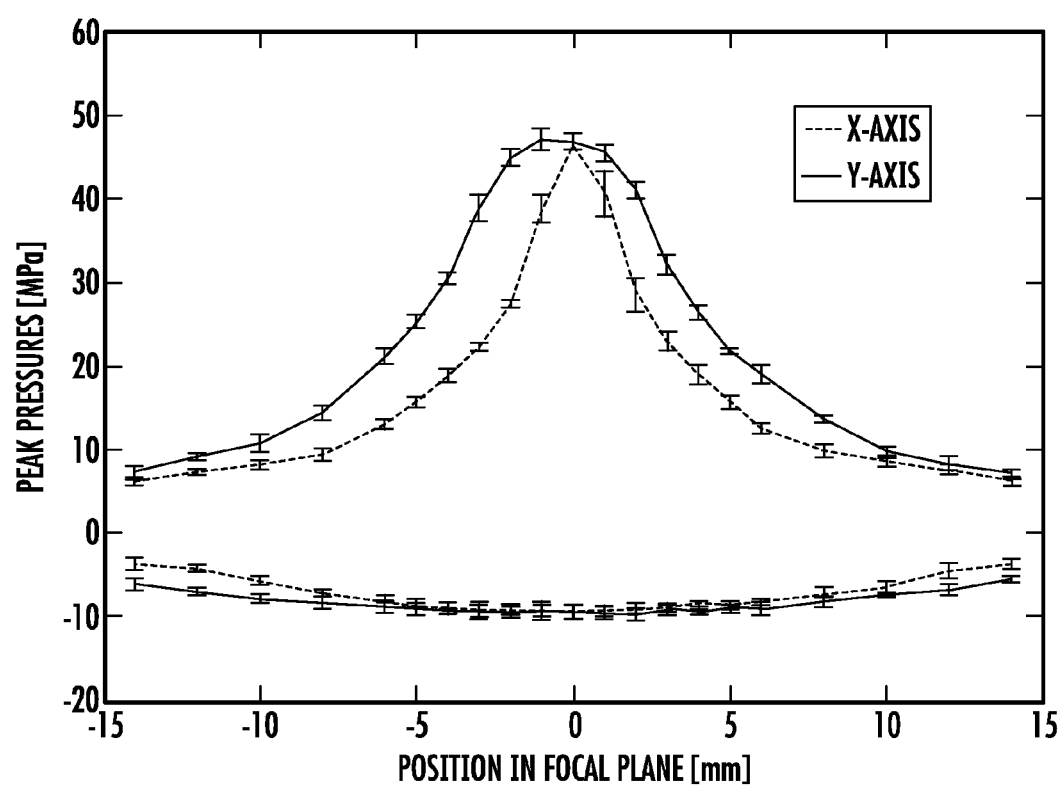
FIG. 4 is a graph showing a pressure distribution along the X- and Y-axis, showing an enlarged beam size along the axis of the barrier materials.

By way of specific example, an acoustic barrier 300 comprising a plurality of non-deformable elements 310 can be used for the generation of a non-axisymmetric pressure distribution having an elliptical shape that has a broader beam size along the major axis of the ellipse. A pair of non-deformable elements 310 can comprise acoustic barrier materials, such as cork, and can be arranged to block fan-shaped areas on the coil surface of a MODULARIS™ shock wave generator. As shown in FIG. 4, using such non-deformable elements 310 can cause a significant increase of the beam size (e.g., from about 7.3 mm to 10.0 mm) along the Y-axis where the barrier materials are placed, as well as a corresponding decrease in the X-axis (e.g., from about 7.3 mm to 5.7 mm). Thus, by changing the size/percentage area ratio (with respect to the original surface area of shock wave source 200) and orientation of non-deformable elements 310, a user can adjust the beam size and steer the beam to rotate around the axis of the lithotripter.

Figure 5B:
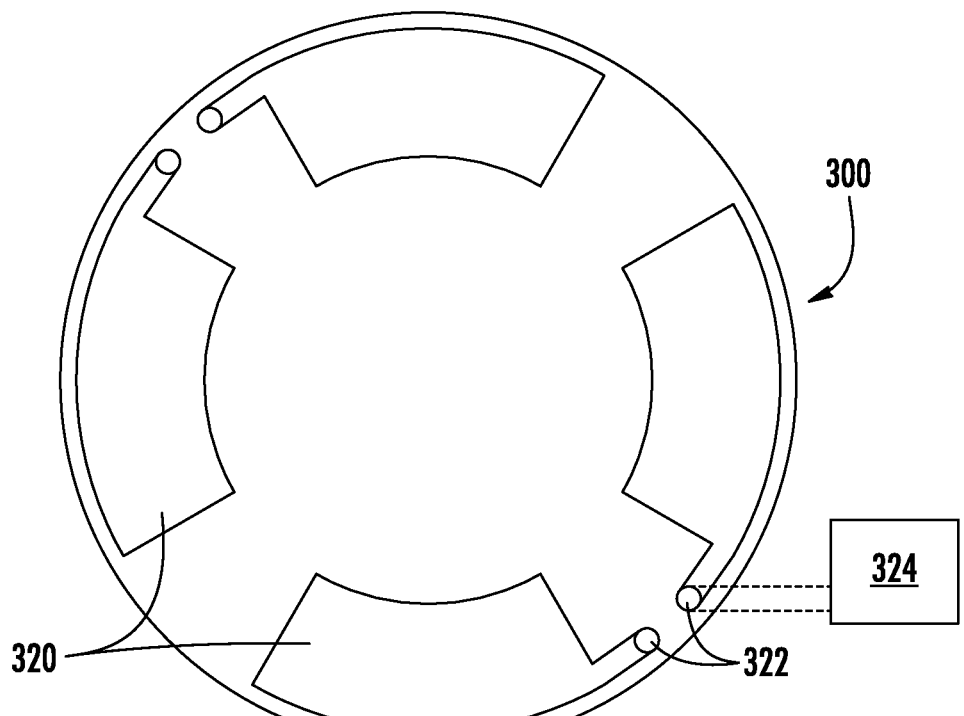
FIG. 5B is a top view of the lithotripter of FIG. 5A.
Figure 5A:
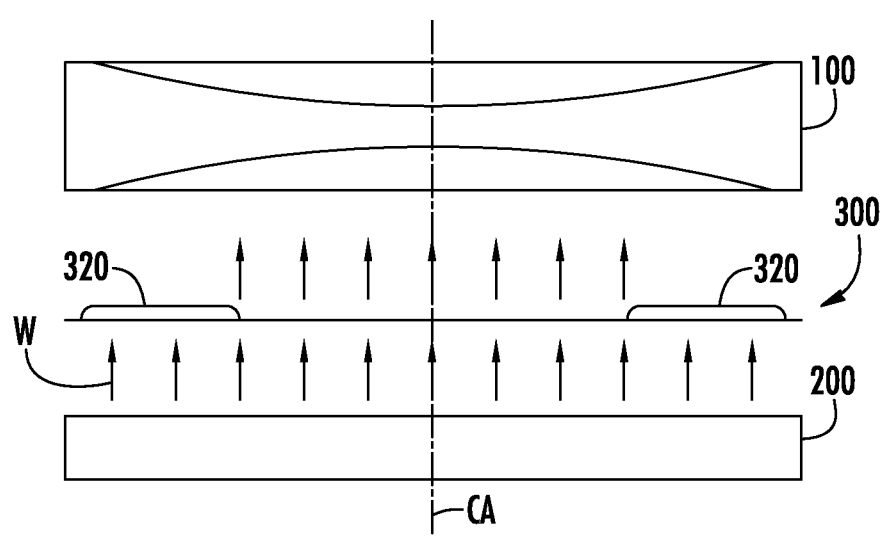
FIG. 5A is a cutaway side view of a lithotripter having an acoustic barrier comprising a plurality of inflatable cavities according to an embodiment of the subject matter disclosed herein.

In another configuration shown in FIGS. 5A and 5B, acoustic barrier 300 can comprise one or more inflatable cavities 320 positioned between acoustic focusing member 100 and shock wave source 200. For instance, acoustic barrier 300 can comprise a deformable membrane that can be positioned against either acoustic focusing member 100 or shock wave source 200 and can be sealed against the adjacent surface at selected places to define one or more individual inflatable cavities 320. For instance, such a membrane can comprise an elastic polymer (e.g., an elastomer) or any other material that will not rupture in response to increased fluid pressure. In one particular configuration, for example, the membrane can be composed of a polyethylene-coated mylar film.

Alternatively, as shown in FIG. 5A, acoustic barrier 300 can be a deformable structure that can be spaced apart from both of acoustic focusing member 100 and shock wave source 200. Even if the structure is spaced apart from acoustic focusing member 100 and shock wave source 200 by only a small distance (e.g., a few mm), such spacing can allow for flow of the surrounding acoustic propagation medium (e.g., degassed water) to cool the surface of shock wave source 200. The deformable structure can be segmented to define one or more inflatable cavities 320. For instance, acoustic barrier 300 can be constructed from two elastic polymer (e.g., elastomeric) membranes that are adhered, fused, or otherwise bonded together along perimeter edges of each of inflatable cavities 320 to define the individual cavities. In a further configuration, inflatable cavities 320 can be separate structures from each other. Regardless of the particular configuration, each of inflatable cavities 320 can have a port such as port 322, which can be connected to a fluid source 324. In this way, an acoustically attenuating or reflecting gas (e.g., air) can be introduced through port 322 into a respective one of inflatable cavities 320 to inflate it. When inflated, inflatable cavities 320 can effectively block the passage of at least a portion of shock waves W generated by shock wave source 200 to generate a modified acoustic pressure field.

Similar to the use of non-deformable elements 310 discussed above, any number of inflatable cavities 320 can be provided, and they can be actuated together or individually in any sequence to achieve a desirable modified acoustic pressure field (e.g., a non-axisymmetric pressure field). For example, as shown in FIG. 5A, an opposing pair of inflatable cavities 320 can be inflated together to block portions of shock waves W generated by shock wave source 200 on either side of central axis CA of shock wave source 200. Such an arrangement can produce a non-axisymmetric pressure distribution having a substantially elliptical shape that has a broader beam size along the major axis of the ellipse. The level of eccentricity in the beam size and orientation of its long axis can be controlled by the level of inflation of inflatable cavities 320. In addition, the orientation of the modified acoustic pressure field can be determined by selecting which opposing pairs of inflatable cavities 320 are inflated at a time. As a result, a wide range of beam shapes, sizes, and steering orientation/patterns can be created.

By way of specific example, inflatable cavities 320 made of elastomer or other polymer membranes can be used in selectively blocking different areas around the rim of a MODULARIS™ shock wave source. Selectively blocking different areas around the rim of the MODULARIS™ shock wave source can be accomplished by providing a rapid injection (or suction) of air into (or out of) the array of inflatable cavities 320 one pair at a time. By controlling the pair of cavities to be inflated, the major axis of the elliptical pressure contour can be steered in a particular direction. This feature can be used to align the pressure contour of the lithotripter field with the distribution of the stones in the renal collecting system to improve stone comminution efficiency. For example, the direction of the broader beam size can be aligned either with upper-to-lower pole or pelvis-to-ureter direction of the kidney, depending on the geometry and distribution of stones revealed by fluoroscopy. To match with kidney movement due to respiratory motion (largely along a direction in parallel to the spine), the broad beam size can be aligned with the upper-to-lower pole direction, and wobbled within ±30° during the treatment.

Figure 6B:
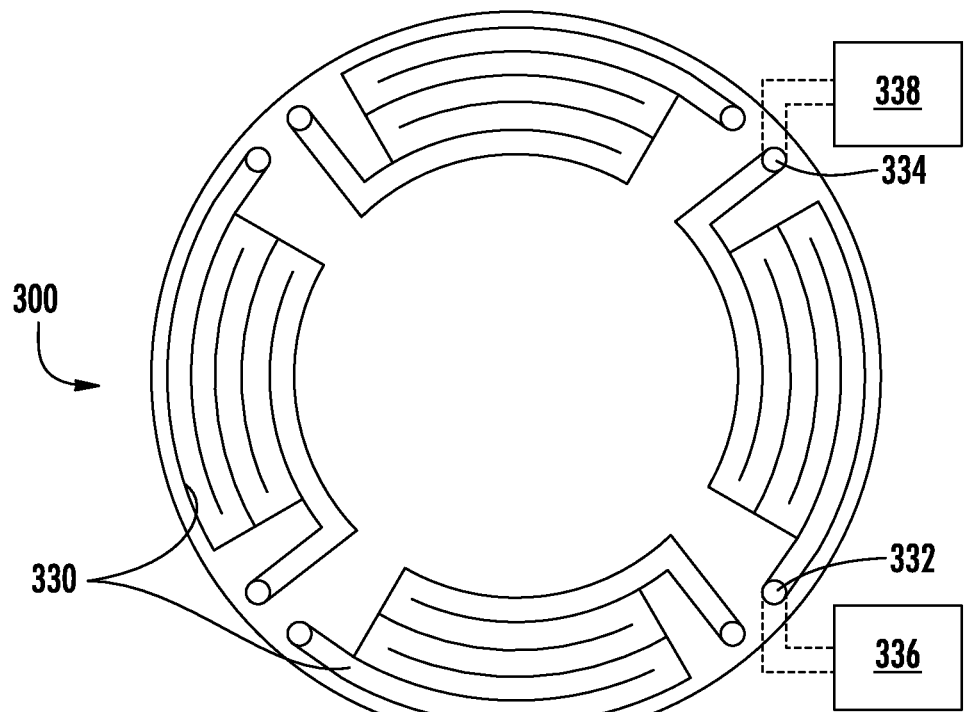
FIG. 6B is a top view of the lithotripter of FIG. 6A.
Figure 6A:
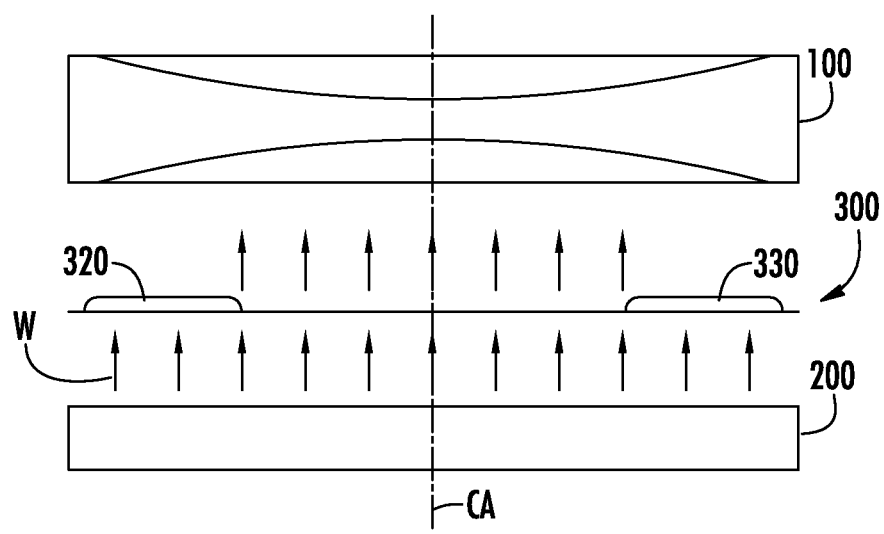
FIG. 6A is a cutaway side view of a lithotripter having an acoustic barrier comprising a plurality of inflatable channels according to an embodiment of the subject matter disclosed herein.

In yet another particular configuration shown in FIGS. 6A and 6B, acoustic barrier 300 can comprise one or more inflatable channels 330 positioned between acoustic focusing member 100 and shock wave source 200. Inflatable channels 330 can be constructed similarly to inflatable cavities 320 shown in FIGS. 5A and 5B. Specifically, inflatable channels 330 can be formed by an deformable membrane that can be positioned against either acoustic focusing member 100 or shock wave source 200, or they can be formed in an deformable structure that can be positioned between acoustic focusing member 100 and shock wave source 200. In contrast to inflatable cavities 320, however, inflatable channels 330 can define a serpentine, maze-like, or otherwise winding path between a first port 332 and a second port 334.

In this arrangement, when it is desired to block a portion of shock waves W generated by shock wave source 200, an acoustically attenuating or reflecting gas (e.g., air) can be introduced through either first port 332 or second port 334 to fill a respective one of inflatable channels 330, thereby blocking the desired portion of shock waves W, and generating a modified acoustic pressure field. When it is desired to allow that portion of shock waves W to pass through acoustic barrier 300 unblocked, an acoustically transmissive fluid can be introduced through either first port 332 or second port 334 into a respective one of inflatable channels 330, thereby forcing the acoustically attenuating or reflecting gas out through the other of first port 332 or second port 334. For example, air can be pumped into inflatable channels 330 when blocking is desired, and degassed water can be pumped into inflatable channels 330 to force the air out when unblocked transmission is desired. Alternatively, rather than being a one-way conduit, first port 332 can be connected to a first fluid source 336 containing an attenuating or reflecting fluid (e.g., air), and second port 334 can be connected to a second fluid source 338 containing a transmissive fluid (e.g., degassed water). In this arrangement, the attenuating or reflecting fluid can be provided via first port 332, and the transmissive fluid can be provided via second port 334.

Figure 7C:
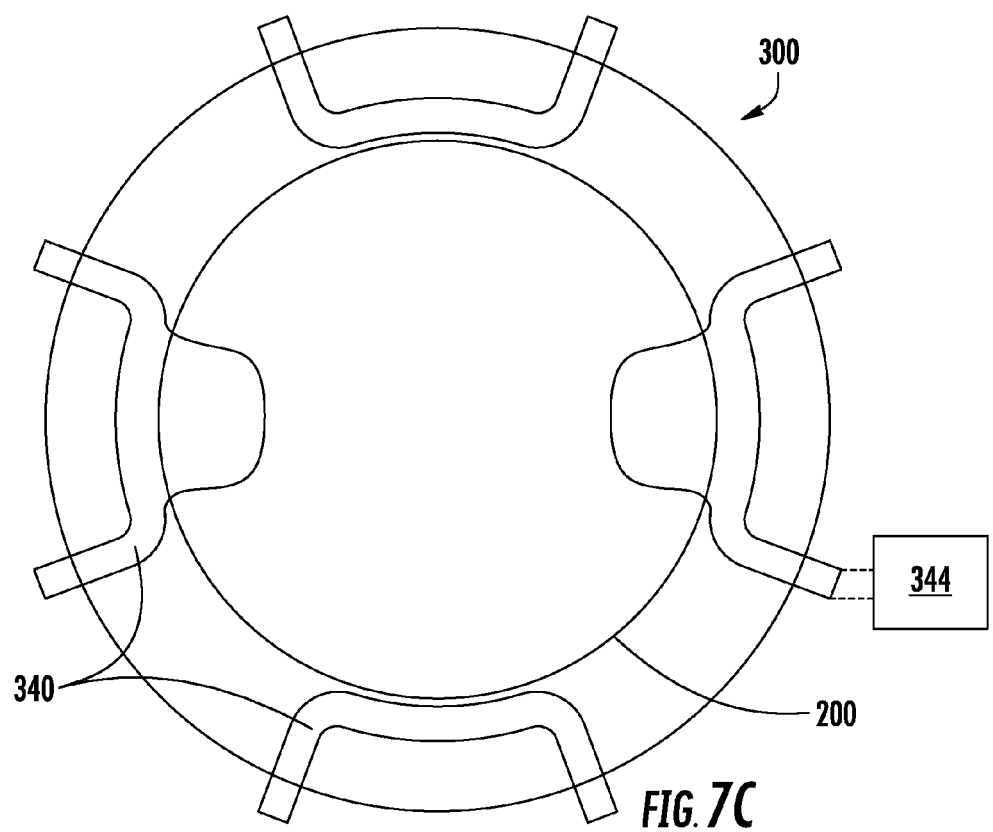
FIG. 7C is a top view of the lithotripter of FIG. 7A.
Figure 7A:
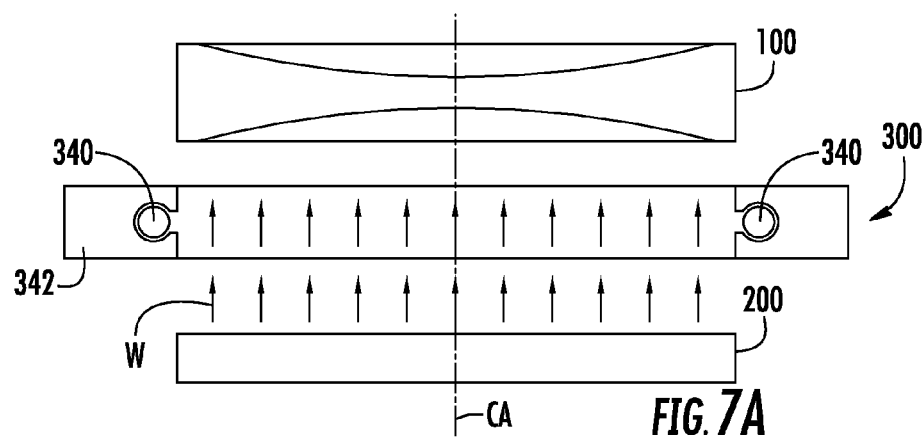
FIGS. 7A and 7B are cutaway side views of a lithotripter having an acoustic barrier comprising a plurality of inflatable tubes in two different operating configurations according to an embodiment of the subject matter disclosed herein.
Figure 7B:
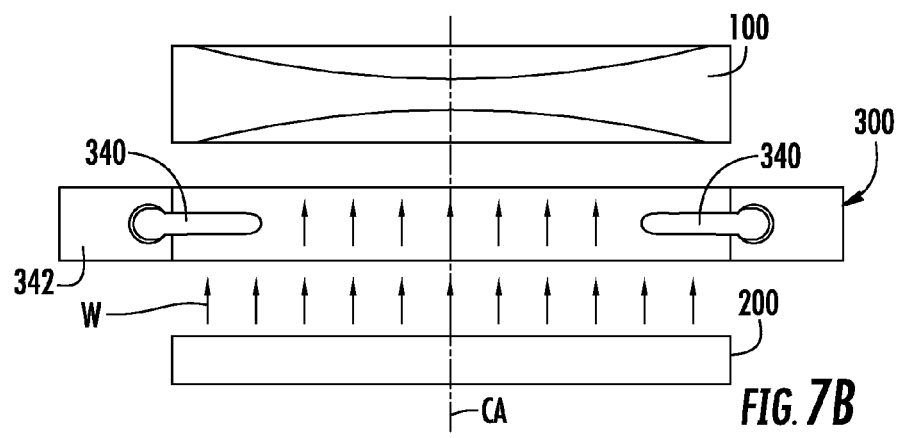

In still another particular configuration shown in FIGS. 7A through 7C, acoustic barrier 300 can comprise one or more inflatable tubes 340 positioned between acoustic focusing member 100 and shock wave source 200 about the perimeter of shock wave source 200. Inflatable tubes such as tubes 340 can be constrained at predetermined points by a frame 342. Inflatable tubes 340 can be connected to a fluid source 344 (e.g., at an end of inflatable tubes 340). In this way, an acoustically attenuating or reflecting gas (e.g., air) can be introduced through port 344 into a respective one of inflatable tubes 340 to inflate portions of inflatable tubes 340 that are not constrained by frame 342. As shown for example in FIG. 7B, the inflated portions of inflatable tubes 340 can extend inward toward central axis CA of shock wave source 200 to block the passage of at least a portion of shock waves W generated by shock wave source 200, and generate a modified acoustic pressure field. As with other configurations discussed above, the number and spacing of inflatable tubes 340, as well as the specific configuration of which sections of inflatable tubes 340 are constrained by frame 342, can be varied to control the final shape of the modified acoustic pressure field.

The subject matter disclosed herein can be embodied in other forms without departure from the spirit and essential characteristics thereof. The aspects and embodiments described therefore are to be considered in all respects as illustrative and not restrictive. Other aspects and embodiments that are apparent to those of ordinary skill in the art are also within the scope of the subject matter disclosed herein.

What is claimed is:

1. A lithotripter apparatus for producing a steerable acoustic pressure field, the lithotripter apparatus comprising:
   a shock wave source configured to generate a shock wave having a axisymmetric acoustic pressure field;
   an acoustic focusing member positioned for receiving the shock wave prior to the shock wave traveling to a target; and
   an acoustic barrier positioned between the shock wave source and the acoustic focusing member, the acoustic barrier configured to selectively block a portion of the shock wave generated by the shock wave source such that the axisymmetric pressure field is transformed into a modified acoustic pressure field;

wherein the acoustic barrier comprises:

one or more frames positioned about a perimeter edge of the shock wave source; and a plurality of inflatable channels constrained by the one or more frames, each of the inflatable channels comprising a first port and a second port for connection to one or more fluid sources, wherein the plurality of inflatable channels are selectively inflatable in a direction extending toward a central axis of the shock wave source.

2. The lithotripter apparatus according to claim 1, wherein the one or more frames comprise an even number of frames spaced at regular intervals about a central axis of the shock wave source.

3. The lithotripter apparatus according to claim 1, wherein the inflatable channels are formed in a deformable membrane positioned against the shock wave source.

4. The lithotripter apparatus according to claim 1, wherein the inflatable channels are formed in a deformable structure that is spaced apart from the shock wave source and the acoustic focusing member.

5. The lithotripter apparatus according to claim 1, wherein the modified acoustic pressure field comprises a non-axisymmetric pressure field having an elliptical shape.

6. The lithotripter apparatus according to claim 1, wherein the shock wave source comprises a source selected from the group consisting of an electromagnetic shock wave source, an electrohydraulic shock wave source, and a piezoelectric shock wave source.

* * * * *